United States Patent [19]

Möller et al.

[11] Patent Number: 4,545,984

[45] Date of Patent: Oct. 8, 1985

[54] ARENE-CARBOXYLIC ACID DERIVATIVES AS ANTISEBORRHEIC ADDITIVES FOR COSMETIC AGENTS

[75] Inventors: Hinrich Möller; Siegfried Wallat, both of Monheim; Friedhelm Bartnik, Dusseldorf, all of Fed. Rep. of Germany

[73] Assignee: Henkel Kommanditgesellschaft auf Aktien, Duesseldorf, Fed. Rep. of Germany

[21] Appl. No.: 444,587

[22] PCT Filed: May 21, 1982

[86] PCT No.: PCT/EP82/00109

§ 371 Date: Nov. 15, 1982

§ 102(e) Date: Nov. 15, 1982

[87] PCT Pub. No.: WO82/04189

PCT Pub. Date: Dec. 9, 1982

[30] Foreign Application Priority Data

May 27, 1981 [DE] Fed. Rep. of Germany ....... 3121064

[51] Int. Cl.[4] .................... A61K 7/06; A61K 31/235
[52] U.S. Cl. ...................... 424/70; 514/532; 424/DIG. 4
[58] Field of Search ............ 424/70, 308, 60, DIG. 4; 560/64

[56] References Cited

U.S. PATENT DOCUMENTS

| 3,076,017 | 1/1963 | Grisley | 260/474 |
| 3,317,382 | 5/1967 | Brunner et al. | 514/159 |
| 3,766,245 | 10/1973 | Hausermann et al. | 260/473 R |
| 3,868,406 | 2/1975 | Siddall | 260/473 R |
| 4,136,165 | 1/1979 | Möller et al. | 424/60 |
| 4,235,889 | 11/1980 | Evers | 424/195 |

FOREIGN PATENT DOCUMENTS

| 524131 | 5/1954 | Belgium. |
| 802042 | 1/1974 | Belgium. |
| 0054174 | 6/1982 | European Pat. Off. ............ 424/308 |
| 2617817 | 11/1974 | Fed. Rep. of Germany. |
| 893112 | 5/1944 | France. |
| 57704 | 6/1946 | Netherlands. |
| 561544 | 5/1975 | Sweden. |

*Primary Examiner*—Sidney Marantz
*Assistant Examiner*—Shawn P. Foley
*Attorney, Agent, or Firm*—Ernest G. Szoke; Nelson Littell, Jr.; Henry E. Millson, Jr.

[57] ABSTRACT

The invention concerns cosmetic agents containing compounds of the general formula (I)

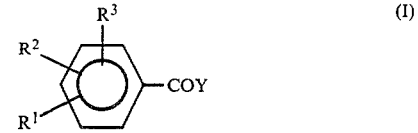

in which $R^1$, $R^2$ and $R^3$ represent independently of one another a hydrogen atom, an intermediate alkyl group with 3 to 10 carbon atoms, a halogen atom, preferably a chlorine atom, a hydroxy group, an aryl group, an alkoxy group with 1 to 20 carbon atoms, substituted, if needed, with aryl, hydroxy, amino, alkoxy as well as aryloxy groups, or a carboxyl group esterified with an intermediate-chain alkyl group with 2 to 12 carbon atoms or with an aralkyl group, or two of the radicals $R^1$—$R^3$ represent a naphthalene ring together with the benzene ring, and Y stands for an alkoxy group with 1 to 12 carbon atoms or an aralkoxy group. The compounds are used in amounts of 0.01 to 20, preferably 1 to 10, percent by weight, calculated with regard to the total preparation.

9 Claims, No Drawings

ARENE-CARBOXYLIC ACID DERIVATIVES AS ANTISEBORRHEIC ADDITIVES FOR COSMETIC AGENTS

The subject of the invention are topical cosmetic preparations for the improvement of the oily and unesthetic appearance of hair and skin, especially for the treatment of very oily hair.

The excessive secretion of the seborrheic glands of the scalp gives the hair an oily appearance which is generally considered unesthetic. Consequently, many attempts were made to restore a healthy appearance to the hair by adjusting the secretion of the seborrheic glands to their normal level with suitable preparations. Oral preparations containing cysteamine derivatives were recommended for the treatment of seborrhea in the DE-OS No. 1667902. Shampoos with sulfur, mercury or tar additives were used to treat seborrhea of the hair on the head. It was observed that the extended use of these well-known products frequently led to side effects without producing actually satisfactory results with regard to efficacy or application technological properties. Finally, N,N-diethyl-m-toluamide was recommended as active substance for the treatment of dandruff due to seborrhea in the DE-OS No. 1906665. In the U.S. Pat. No. 3,755,604, phenyl-pentadienoic acids are recommended as agent for the prevention of the production of sebum. But it was found that neither N,N-diethyl-m-toluamide nor phenyl-pentadienoic acid has a satisfactory antiseborrheic effect.

Now, it was observed that topical cosmetic preparations with a content of compounds of the general formula:

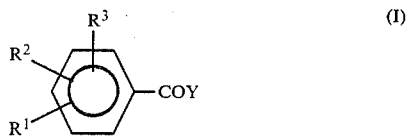

in which $R^1$, $R^2$ and $R^3$ represent independently of one another a hydrogen atom, an intermediate alkyl group with 3 to 10 carbon atoms, a halogen atom, preferably a chlorine atom, a hydroxy group, an aryl group, an alkoxy group with 1 to 20 carbon atoms substituted, if needed, with aryl, hydroxy, amino, alkoxy as well as aryloxy groups, or a carboxyl group esterified with an intermediate-chain alkyl group with 2 to 12 carbon atoms or an aralkyl group, as well as two of the radicals $R^1$—$R^3$ can represent a naphthalene ring together with the benzene ring, and Y represents an alkoxy group with 1 to 12 carbon atoms or an aralkoxy group, are especially effective in the treatment of seborrheic skin and very oily hair.

The compounds of formula (I) are known from the literature and most of them are commercially available, or their precursors are generally commercially available. When only the arene-carboxylic acids are available as precursors of the compounds, these can be converted into the respective esters by well-known methods of organic chemistry. For the synthesis of the alkoxy-substituted arene-carboxylic acid derivatives, the best approach is the alkylation of arene-carboxylic acid esters containing the phenolic hydroxyl group with suitable alkylating agents. Especially suitable for the introduction of multisubstituted alkoxy groups are epihalohydrins, which are then reacted with different or the same nucleophiles.

Arene-carboxylic acids from which the compounds to be used according to the invention are prepared are, for example: 4-Propyl-, 4-butyl-, 4-tert-butyl-, 4-octyl-, 4-decyl-, 4-phenyl-, 4-methoxy-, 3-methoxy-, 2-methoxy-, 3,4-dimethoxy-, 2,4-dimethoxy-, 3,4,5-trimethoxy-, 2,4,6-trimethoxy-, 4-propoxy-, 4-hexyloxy-, 4-decyloxy-, 4-tetradecyloxy-, 4-benzyloxy-, 4-(3,4-dimethoxybenzyloxy)-, 4-(3-phenoxy-2-hydroxypropoxy)-, 4-(3-(4-methoxyphenoxy)-2-hydroxypropoxy)-, 4-(3-(3,4-dimethoxyphenoxy)2-hydroxy-propoxy)-, 4-(3-(4-chlorophenoxy)-2-hydroxypropoxy)-, 4-(3-(3,4-dichloroanilino)-2-hydroxypropoxy)-, 4-chloro-, 3,4-dichloro-, 2,4-dichloro-, 2,5-dichloro-, 2,4,5-trichloro-, 4-bromo-, 5-chloro-2-methoxy-benzoic acid, phthalic acid, 4,5-dichlorophthalic acid, benzoic acid, α-naphthoic acid, β-naphthoic acid, isophthalic acid, terephthalic acid.

Suitable alcohol components for the preparation of the arene-carboxylic acid esters to be used according to the invention are, for example:
Methanol, ethanol, propanol, isopropanol, n-butanol, isobutanol, sec-butanol, tert-butanol, pentanol, hexanol, octanol, 2-ethylhexanol, decanol, benzyl alcohol.

The cosmetic agents according to the invention are solutions of the active compounds of Formula (I) to be used in water, in alcohol, in aqueous alcoholic mixtures, in oil, suspensions, gels, emulsions, ointments, pastes or aerosols. The antiseborrheic arene-carboxylic acid esters can be incorporated in almost all cosmetic agents normally used for the treatment of skin and hair, for example in hair tonics, shampoos, hair treatments, hair rinses, or also in skin lotions and shaking mixtures. In addition to the compounds of Formula (I), the products according to the invention contain known vehicles and adjuvants such as water, organic solvents, surfactants, oils and fats, waxes, perfume oils, pigments, preservatives and similar substances. Shampoo is an advantageous form of application for the treatment of very oily hair. In addition to the sebosuppressive active agent, such shampoos may contain anionic, cationic, nonionic or amphoteric tensides, pigments, fragrances, thickeners or conditioners.

The cosmetic agents according to the invention contain the arene-carboxylic acid derivatives in an amount of 0.01 to 20 percent by weight, preferably 1 to 10 percent by weight, calculated with regard to the total product. The agents according to the invention can be applied daily; but satisfactory results are obtained even with one weekly application. The individual dose to be used for each treatment is not critical. Undesirable side effects were not observed. The oily appearance of the hair is reduced and renewed oiliness is delayed, which makes normal hair grooming possible. A lasting improvement in the appearance of the skin is possible with regular applications of the agents according to the invention in the form of skin creams or milk preparations or shaking mixtures.

The following examples shall explain the subject of the invention in more detail.

EXAMPLES

First, the preparation of the arene-carboxylic acid esters to be used according to the invention is described with an example.

(A) Ethyl-3,4-Dichlorobenzoate

A mixture of 42 g (0.2 mol) 3,4-dichlorobenzoyl chloride and 200 ml ethanol was heated to boiling for 2 hours, evaporated, the residue taken up in ether, the solution washed with NaHCO$_3$-solution and water, dried and evaporated. The distillation yielded 32 g (73% theor.) ethyl-3,4-dichlorobenzoate with a BP of 84° C./0.13 mbar and a mp of 33° to 35° C.

The following, additional compounds with the formula (I) were prepared in an analogous manner:

(B) Methyl-4-Decyloxybenzoate
    mp: 45°–46° C.
(C) Ethyl Biphenylyl-4-Carboxylate
    mp: 46°–48° C.
(D) Ethyl-4-Benzyloxybenzoate
    mp: 43°–45° C.
(E) Methyl-4-(3-(4-Chloroanilino)-2-Hydroxypropoxy)-Benzoate
    mp: 126° C.
(F) Methyl-4-(3-(4-Chlorophenoxy)-2-Hydroxypropoxy)-Benzoate
    mp: 86°–88° C.
(G) Bis-2-Ethylhexyl Phthalate
    mp: 384° C./1000 mbar; $n_D^{20}$: 1.4853

The antiseborrheic action of the compounds used in the cosmetic preparations according to the invention was subjected to closer scrutiny in subsequent animal experiments. Male Wistar rats weighing 220–230 g were used as experimental animals. The degree of brown discoloration on the shaved backs of the rats was visually evaluated. The brown discoloration is caused by the brown skin surface lipid of the rats. This test is based on the observation that young female rats as well as male rats after washing with tenside solution or a lipolytic solvent, and also male rats that had been systemically treated with estrogen, have only normal, fair, pink-colored skin showing after shaving; in keeping with this observation, comparatively negligible amounts of lipid can be extracted from the shaved hair.

For the evaluation of the sebosuppressive effect, the test substances A, B, C, D, E, F and G were applied each in the form of a 1% solution in ethanol or ethanol/acetone (1:1) by brushing unilaterally on the back hair of groups of six rats. The other side was treated only with the solvent minus active substance (control side).

During the 14 days of testing, one daily application was made on a total of nine days. A group of six rats that remained completely untreated was used as additional control. At the end of the testing, the animals were shaved on backs and flanks, and independently visually examined under double blind conditions by an evaluating panel (6 persons).

The first criterion was the evaluation of the correct identification of the treated side by the majority of the panelists. The following differentiation was made:

| Symbol | Percentage of panelists who recognized an effect |
| --- | --- |
| ++ | 100% |
| + | >50%, 100% |
| 0 | ≦50% |

The second criterion was the determination of the difference between right and left side, for which 1 point could be given per panelist and animal, the darker side being graded 1, the higher side 0, and in the case of uniform appearance, both sides 0.5 each.

The third criterion was the additional classification of the differences in the intensity of the brown coloring, using the following scale:

3 points dark brown
2 points medium brown
1 point weakly brown
0 points no brown discoloration Significant differences between untreated and treated side in the second method of evaluation indicate the topical effectiveness of a substance. The third method of evaluation is used to form the differences of the sums of points between the untreated control animals and respectively the treated and untreated sides of the experimental animal groups, significant differences between control animals and the treated side of the experimental animals again denoting the action of a substance.

Parallel to the above, a distinct difference between the untreated and the treated side of the experimental animal groups usually can be seen. But this difference is not always as distinct as that between control animals and treated side, which may have different reasons, such as mechanical transfer of substance from one side to the other, or influence of the solvent. The following plan was used for the differentiation of the effects according to the evaluation methods 2 and 3.

| Symbol | Point difference |
| --- | --- |
| ++ | very large (>99.9% probability) |
| + | significant (≧95% probability) |
| (+) | pronounced but <95% probability |

The results of the evaluation by the above-mentioned plan for the tested substances are compiled in the following table.

| | Evaluation of the Sebosuppressive Effects | | |
| --- | --- | --- | --- |
| | Method of evaluation | | |
| Substance | 1 | 2 | 3 |
| A | ++ | ++ | + |
| B | ++ | ++ | ++ |
| C | ++ | ++ | + |
| D | + | + | + |
| E | + | + | ++ |
| F | + | + | ++ |
| G | + | + | ++ |
| N,N—Diethyl-m-toluamide (DE-OS No 1906665) | + | (+) | (+) −0 |
| ⌬—⋀—CO$_2$H (U.S. Pat. No. 3,755,604) | 0 | 0 | + |

Following are examples of topical agents according to the invention for the treatment of very oily hair and seborrheic skin:

| | Percent by weight |
| --- | --- |
| Hair Thickener | |
| Ethanol, 96% | 45.0 |
| Ethoxylated, saturated fatty alcohol | 0.20 |
| Luviset ® | 3.50 |
| 2-Hydroxy-4-methoxybenzophenone | 0.05 |
| Cationic emulsifying agent | 0.10 |
| Cationic tenside | 1.20 |
| Perfume oil | 0.15 |
| Compound A | 5.50 |

| | Percent by weight |
|---|---|
| Water | 43.30 |
| Hair Treatment | |
| Tegin M ® (glyceryl mono- and distearate) | 0.7 |
| Cationic tenside | 2.0 |
| Cholesterol | 0.2 |
| Soy lecithin | 0.3 |
| Emulgade A ® (mixture of cetyl-stearyl alcohol with nonionic emulsifying agents) | |
| Perfume oil | 0.3 |
| Compound B | 7.0 |
| Water, completely demineralized | 81.5 |
| Skin Cream | |
| Self-emulsifying mixture of mono-diglycerides of higher, saturated fatty acids with potassium stearate ® Dehydag | 16 |
| Cetyl-stearyl alcohol with approx. 12 mols ethylene oxide | 1.0 |
| 2-Octyldodecanol | 6.0 |
| Isopropyl myristate | 4.0 |
| Glycerol | 6.0 |
| Compound D | 7.0 |
| Water | 60.0 |

We claim:

1. A process for reducing sebaceous cell sebum production in a mammal in need thereof which comprises contacting said sebaceous cell in the skin of said mammal with an effective amount to reduce sebum production of at least one compound of the formula (I):

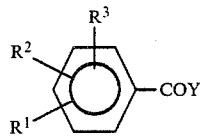

in which $R^1$, $R^2$ and $R^3$ represent independently of one another an alkoxy with 1 to 20 carbon atoms, or an alkoxy with 1 to 20 carbon atoms substituted with hydroxy, phenyl, or alkoxy as well as aryloxy, and Y represents an alkoxy with 1 to 12 carbon atoms or aralkoxy.

2. A process for reducing sebaceous cell sebum production in a mammal in need thereof which consists essentially of contacting said sebaceous cell in the skin of said mammal with an effective amount to reduce sebum production of at least one compound having the formula

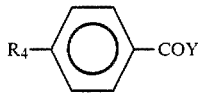

wherein $R_4$ represents a member selected from the group consisting of alkoxy having 1 to 20 carbon atoms and alkoxy having 1 to 20 carbon atoms substituted with at least one substituent selected from the group consisting of hydroxy, phenyl, 3,4-dimethoxyphenyl, phenoxy, 4-methoxyphenoxy, 3,4-dimethoxyphenoxy and 4-chlorophenoxy, and Y represents an alkoxy having from 1 to 10 carbon atoms.

3. The process of claim 2 wherein $R_4$ is decyloxy and Y is methoxy.

4. The process of claim 2 wherein $R_4$ is benzyloxy and Y is ethoxy.

5. The process of claim 2 wherein $R_4$ is 3-(4-chlorophenoxy-2-hydroxy-propoxy and Y is methoxy.

6. A topical cosmetic preparation for the treatment of seborrhea containing an antiseborrheically effective amount of a compound having the formula

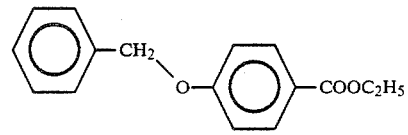

as an antiseborrheic, and further containing conventional vehicles and additives for topical application.

7. The topical cosmetic preparation of claim 6 wherein said antiseborrheically effective amount is from 1 to 10 percent by weight in said topical cosmetic preparation.

8. A topical cosmetic preparation for the treatment of seborrhea containing an antiseborrheically effective amount of a compound having the formula

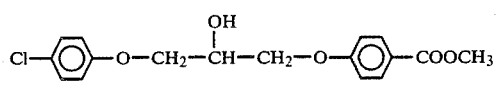

as an antiseborrheic, and further containing conventional vehicles and additives for topical application.

9. The topical cosmetic preparation of claim 8 wherein said antiseborrheically effective amount is from 1 to 10 percent by weight in said topical cosmetic preparation.

* * * * *